United States Patent [19]

Reedy

[11] Patent Number: 4,688,936
[45] Date of Patent: Aug. 25, 1987

[54] MATRIX ISOLATION APPARATUS WITH EXTENDED SAMPLE COLLECTION CAPABILITY

[75] Inventor: Gerald T. Reedy, Bourbonnais, Ill.

[73] Assignee: Cryolect Scientific Corporation, Bourbonnais, Ill.

[21] Appl. No.: 707,156

[22] Filed: Mar. 1, 1985

[51] Int. Cl.[4] .................. G01N 1/22; G01N 21/01; G01N 21/55
[52] U.S. Cl. .................. 356/36; 250/338; 250/341; 250/352; 356/244; 422/89
[58] Field of Search .................. 356/244, 36, 38; 250/338 R, 341, 304, 352, 443.1, 288 A; 422/89; 464/7, 17, 24

[56] References Cited

U.S. PATENT DOCUMENTS

| 4,158,772 | 6/1979 | Reedy | 250/343 |
| 4,594,226 | 6/1986 | Reedy | 422/89 |

FOREIGN PATENT DOCUMENTS

| 2373062 | 8/1978 | France | 356/36 |
| 53-72297 | 6/1978 | Japan | 250/443.1 |

Primary Examiner—Vincent P. McGraw
Attorney, Agent, or Firm—Emrich & Dithmar

[57] ABSTRACT

A gas-sample collection device provides for the matrix isolation of increased amounts of a sample material for spectrographic analysis from a gas chromatographic separation. The device includes an evacuated sample collection chamber containing a disc-like specular carousel having a generally circular lateral surface upon which the sample is deposited in an inert gas matrix for infrared (IR) spectral analysis. The evacuated sample chamber is mounted in a fixed manner and is coupled to and supports a rotating cryostatic coupler which, in turn, supports the specular carousel within the collection chamber. A rotational drive system connected to the cryostatic coupler provides for its rotational displacement as well as that of the sample collecting carousel. In addition, rotation of the cryostatic coupler effects vertical displacement of the carousel to permit the collection of an extended sample band in a helical configuration on the entire lateral surface of the carousel. The various components of the carousel's angular/linear displacement drive system are located exterior to the cryostatic coupler for easy access and improved operation. The cryostatic coupler includes a 360° rotary union assembly for permitting the delivery of a high pressure working fluid to the cryostatic coupler in a continuous flow manner for maintaining the specular carousel at a low temperature, e.g., 10°–20° K., for improved uninterrupted gas sample collection and analysis.

11 Claims, 9 Drawing Figures

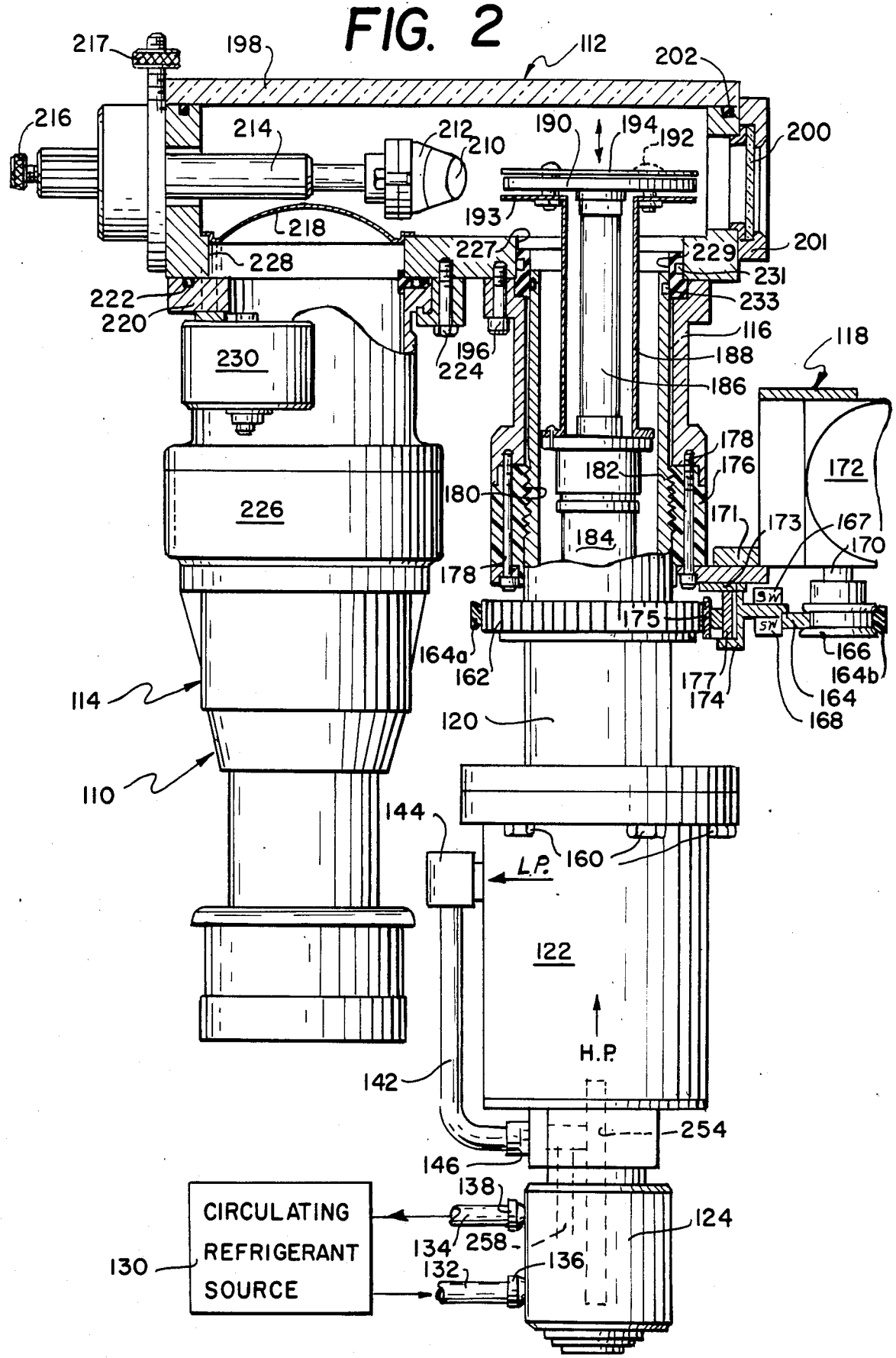

MATRIX ISOLATION APPARATUS WITH EXTENDED SAMPLE COLLECTION CAPABILITY

CROSS REFERENCE TO RELATED APPLICATION

This application is related to but in no way dependent upon the following application which is filed in the name of the present inventor: Ser. No. 583,042, filed Feb. 23, 1984, entitled "Gas Chromatography/Matrix-Isolation Apparatus".

BACKGROUND OF THE INVENTION

This invention relates generally to gas chromatographic/matrix isolation analysis of collected gas samples and is particularly directed to an improved matrix isolation apparatus which affords increased, uninterrupted sample collection and analysis.

Gas chromatographic separations have been useful fundamental tools of chemical research and analysis for some time. The usefulness of this technique is substantially enhanced when the separated components can be conveniently and promptly identified. The matrix isolation technique for presenting samples for spectroscopic examination is also of considerable value in obtaining precise analysis of samples including specific structural information about molecular construction through high resolution infrared analyses. The technique of matrix isolation spectroscopy involves the simultaneous condensation of a gaseous sample in an excess of inert gas to form a solid matrix in which sample molecules are isolated from one another. The technique is powerful in terms of both the variety of species that can be studied and the quality of the spectra that can be obtained. Typically, a particular and distinct sample material is entrapped within a frozen matrix of an inert substance such as argon or krypton. Matrix isolation systems are typically maintained at very low temperatures, such as 10°–20° K. This approach permits the retention of the sample in a neutral and noncontaminating matrix material over an extended period of time. As a result, high resolution infrared (IR) and other spectroscopic types of analyses are available with this approach.

Referring to FIG. 1, there is shown a simplified schematic diagram of a prior art gas chromatography/infrared matrix isolation apparatus 40. A gas chromatography/matrix isolation apparatus as shown in FIG. 1 is described and claimed in Applicant's aforementioned cross referenced related patent application. An earlier version of the improved gas chromatography/matrix isolation apparatus of the aforementioned patent application is described and claimed in U.S. Pat. No. 4,158,772 issued in the name of the present inventor. The contents of the aforementioned patent and patent application are hereby incorporated by reference in the present application.

In the apparatus of FIG. 1, an evacuated cryogenic sample collection chamber 56 contains a specular carousel 64 which may either be provided with a plurality of lateral surfaces or a singular circular surface about the periphery thereof. Positioned adjacent to the evacuated cryogenic sample collection chamber 56 and coupled thereto by means of the combination of a heated delivery line 63 and a nozzle assembly 75 is a gas chromatograph 44. Gas samples for analysis are provided from the gas chromatograph 44 via the heated delivery line 63 and nozzle assembly 75 to the collection chamber 56 for deposit upon the rotating specular carousel 64. The nozzle assembly 75 is positioned within a first port 60 in a lateral portion of the sample collection chamber 56 which includes a window 43 by means of which the deposit of gas sample upon the specular carousel 64 may be observed. A beam of light, e.g., in the IR spectrum, is provided by a light source (not shown) via a second port 74 upon the sample deposited upon the specular carousel 64. The beam is reflected by the sample carrying specular carousel back through a window 78 within the second port and is incident upon a mirror arrangement 65 outside of the sample collection chamber 56. The mirror arrangement directs the reflected IR beam incident thereon to appropriate spectrographic analysis apparatus (not shown).

A vacuum pump 61 is mounted to an upper portion of the sample collection chamber 56 and is coupled thereto via a high vacuum port 59 for the evacuation of the sample collection chamber 56. Rotationally coupled to a lower portion of the sample collection chamber 56 by means of suitable sealant means, such as O-rings 79, is a cryostat/expander module 67. The cryostat/expander module 67 is coupled to and provides support for the specular carousel 64. A rotating joint 66 couples the lower portion of the sample collection chamber 56 to the cryostat/expander module 67 and allows for the rotation of the cryostat/expander module 67 relative thereto. The combination of the cryostat/expander module 67 and the specular carousel 64 rotates together. As the specular carousel 64 rotates, the sample material is deposited from the gas chromatograph 44 via the heated delivery line 63 and the nozzle assembly 75. In practice, the sample material is collected during one rotation of up to 360° of the carousel 64 with the nozzle assembly 75 and IR beam set at one level. The gas flow is stopped. The cryostat/expander module 64 is then rotated appropriately so that the infrared spectra of collected sample material is obtained. The infrared beam and the nozzle assembly 75 are then displaced to a new elevation. The cryostat/expander module 67 is then restored to its starting rotational position. The gas flow and rotational motion are then restored and more material is collected at the new elevation. This is what is accomplished by the screw thread in a slightly different way. This vertical displacement of the nozzle assembly 75 permits the collection of increased amounts of sample material. As vertical displacement of the nozzle assembly 75 changes, the location of sample material deposition along the axis of the gas chromatography/matrix isolation apparatus 40 changes. In order for the IR beam to be incident upon the deposited sample material, the parabolic mirror arrangement 65 must similarly undergo a corresponding displacement by appropriate adjustment means (not shown) for directing the incident IR beam onto the sample material and the reflected IR beam to appropriate spectrographic analysis apparatus.

In this arrangement, the cryostat/expander module 67 is positioned upon a rotary table 69 which, in turn, is positioned upon and supported by a base plate 72. A drive motor 70 is coupled to the rotary table 69 by means of the combination of a drive belt 71 and drive gear 73 for rotationally displacing the rotary table 69. The cryostat/expander module 67 is also coupled to a source of working fluid (not shown) by means of the combination of a working fluid inlet hose 62b and connector 68b and working fluid return hose 62a and connector 68a. The working fluid source thus provides a continuous flow of a working fluid to the cryostat/expander module 67 which, in turn, cools the specular carousel 64 for facilitating sample gas collection thereon. As shown in FIG. 1, during this process the working fluid hoses become wrapped around the cryostat/expander module 67 limiting its rotation and the sample collecting capacity of the gas chromatography/matrix isolation apparatus to one and one-half revolutions of the cryostat/expander module and specular carousel combination. This approach also suffers from limited accuracy in the positioning of the parabolic mirror arrangement for directing the incident IR beam onto the sample material and the reflected IR beam to appropriate spectrographic analysis apparatus.

Applicant's aforementioned patent employs a different approach to increasing the sample collecting capacity of the gas chromatography/matrix isolation apparatus by making use of a spiral-screw shaft within the cryogenic sample collection chamber for vertically displacing the sample collecting carousel. The shaft is in conductive communication with the cold fluid within the cryostat and is thus subjected to the hostile environment of the evacuated cryogenic sample collection chamber. This arrangement imposes restrictions on access to the carousel rotation/translation drive mechanism within the sample collection chamber and results in increased design and operating demands upon the gas chromatography/matrix isolation apparatus and increased cost associated therewith. For example, the aforementioned moving components within the evacuated cryogenic sample collection chamber are highly subject to cold welding, or "galling", and seizure. Materials which might provide good dry lubrication of the carousel threads at cryogenic temperatures do not provide good thermal conductance between the carousel and the source of cooling. In addition, accurate and continuous motion of the carousel is required to collect and identify small quantities of substances delivered by a high resolution gas chromatograph. This accuracy must be on the order of ±0.001 in. (or ±25 μm) which also places very stringent requirements upon the gas sample collection device of the aforementioned patent.

The present invention represents an improvement over the prior art by providing a matrix isolation apparatus with extended sample collection capability. The sample collector drive mechanism of the present invention is positioned exterior to the sample collection chamber and provides for the rotational and linear displacement of the sample collector as well as an expander module upon which the sample collector is mounted. A rotary union assembly couples the expander module to a circulating working fluid source and allows for the continuous rotational displacement of the expander module for virtually any number of revolutions during sample deposition upon the collector while maintaining a sealed coupling between the circulating working fluid source and the expander module.

OBJECTS AND SUMMARY OF THE INVENTION

Accordingly, it is an object of the present invention to provide an improved gas chromatographic/matrix isolation apparatus which affords and increased gas sample collection and analysis capability.

It is another object of the present invention to provide a continuous sample collection and analysis capability in a gas chromatographic/matrix isolation device.

Yet another object of the present invention is to provide an improved arrangement for coupling a continuously rotating low temperature sample collector in a matrix isolation apparatus to a source of continuously circulated, working fluid.

Still another object of the present invention is to provide an improved rotational and translational drive system for a gas sample collecting specular carousel in a gas chromatographic/matrix isolation spectral analysis apparatus.

The present invention contemplates a gas chromatography/matrix isolation device for the spectroscopic analysis of the absorption bands of a vacuum deposited gas sample. An evacuated sample collection chamber contains a disc-shaped specular carousel upon a lateral surface of which the gas sample is deposited via a sample introduction nozzle. The lateral surface of the carousel is irradiated by infrared (IR) radiation and the resulting spectrographic characteristics of the deposited sample may be analyzed.

The specular carousel is mounted to and supported by a cryogenic expander within which a working fluid is continuously circulated for maintaining the specular carousel at a low temperature. The cryogenic expander is rotationally coupled to the sample collection chamber and is displaced by rotational drive means to allow the deposit of a gas sample upon the specular carousel's lateral surface as it is rotated through 360°. In addition, a threaded coupling between the cryogenic expander and the sample collection chamber provides for the vertical displacement of the cryogenic expander, and the specular carousel mounted thereto, as it rotates relative to the sample collection chamber. This permits the full height of the specular carousel's lateral surface to be used for sample collection by angularly displacing the specular carousel beyond 360° and affords increased gas sample collection and analysis. A rotary union in the lower portion of the cryogenic expander is coupled to a circulating working fluid source and permits the continuous rotation of the cryogenic expander as well as the specular carousel mounted thereto through 360° during gas sample deposition and spectral analysis.

BRIEF DESCRIPTION OF THE DRAWINGS

The appended claims set forth those novel features which characterize the invention. However, the invention itself, as well as further objects and advantages thereof, will best be understood by reference to the following detailed description of a preferred embodiment taken in conjunction with the accompanying drawings, where like reference characters identify like elements throughout the various figures, in which:

FIG. 2 is a partially cutaway side view of a gas chromatography/matrix isolation apparatus with extended sample collection capability in accordance with the present invention;

FIG, 8 is a sectional view of the matrix isolation apparatus of FIG. 4 taken along sight line 8—8 therein.

DETAILED DESCRIPTION OF THE PREFERRED EMBODIMENT

Figure 1:
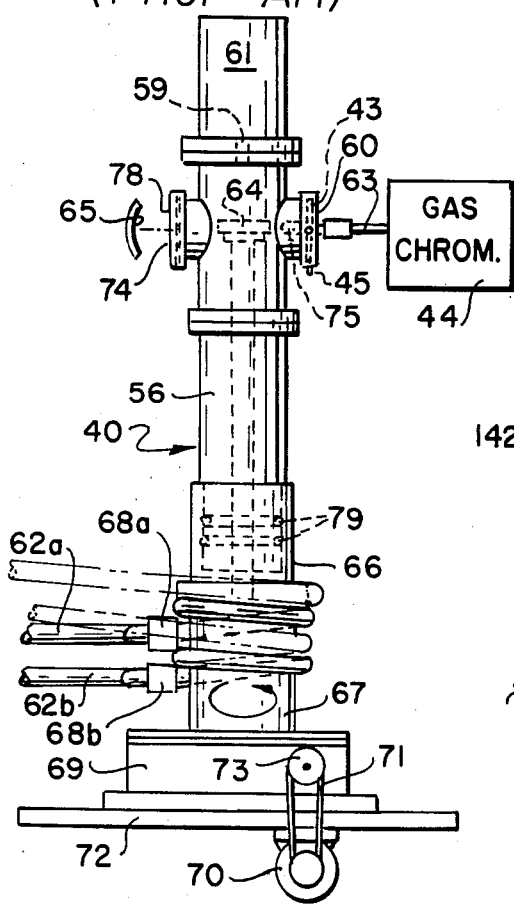
FIG. 1 is a simplified schematic diagram of a prior art gas chromatography/matrix isolation apparatus.

Referring to FIG. 2, there is shown a partially cutaway side view of a matrix isolation apparatus 110 in accordance with the present invention.

The matrix isolation apparatus 110 includes a sample collection chamber 112 into which the gas sample to be analyzed is directed for irradiation by an infrared (IR) beam. The sample collection chamber 112 may be securely coupled to a supporting structure (not shown) by conventionaly means for supporting the matrix isolation apparatus 110. Coupled to and suspended from a lower portion of the sample collection chamber 112 is a vacuum pump 114 for effecting the evacuation thereof. Also coupled and suspended from a lower portion of the sample collection chamber 112 is an expander module 122. The expander module 122 is of a closed cycle helium working fluid type which is provided thereto via a rotary union assembly 124 by a circulating working fluid source 130. The expander module 122 is coupled to and supports lower and upper cryostat duct/support shafts 184, 186 which, in turn, are coupled to and support a specular carousel 190 within the sample collection chamber 112. The gas sample to be analyzed is deposited upon a lateral, circular surface of the disc-shaped specular carousel 190 for analysis as described in detail below.

More specifically, a lower portion of the sample collection chamber 112 is provided with a first aperture 228. Positioned around the first aperture 228 and adjacent thereto is a mounting plate 220 which is held in place on the sample collection chamber 112 by means of a plurality of mounting bolts 224. The mounting plate 220 engages an upper end portion of a vacuum pump housing 114. The pump housing 114 in a preferred embodiment is provided with and includes a turbo pump 226 for producing a high vacuum within the sample collection chamber 112. In addition, a diffusion pump 230 may also be coupled to and supported by the mounting plate 220 for generating a vacuum within the sample collection chamber 112 as an alternative to operation of the turbo pump 226. Secured to an inner portion of the sample collection chamber 112 and positioned over the first aperture 228 therein is a screen 218 for preventing residue within the sample collection chamber from entering the turbo pump 226 and damaging the rotating blade assemblies (not shown) therein. An O-ring, or gasket, 222 is positioned between the mounting plate 220 and the lower surface of the sample collection chamber 112 for improved sealing engagement therebetween.

Figure 3:
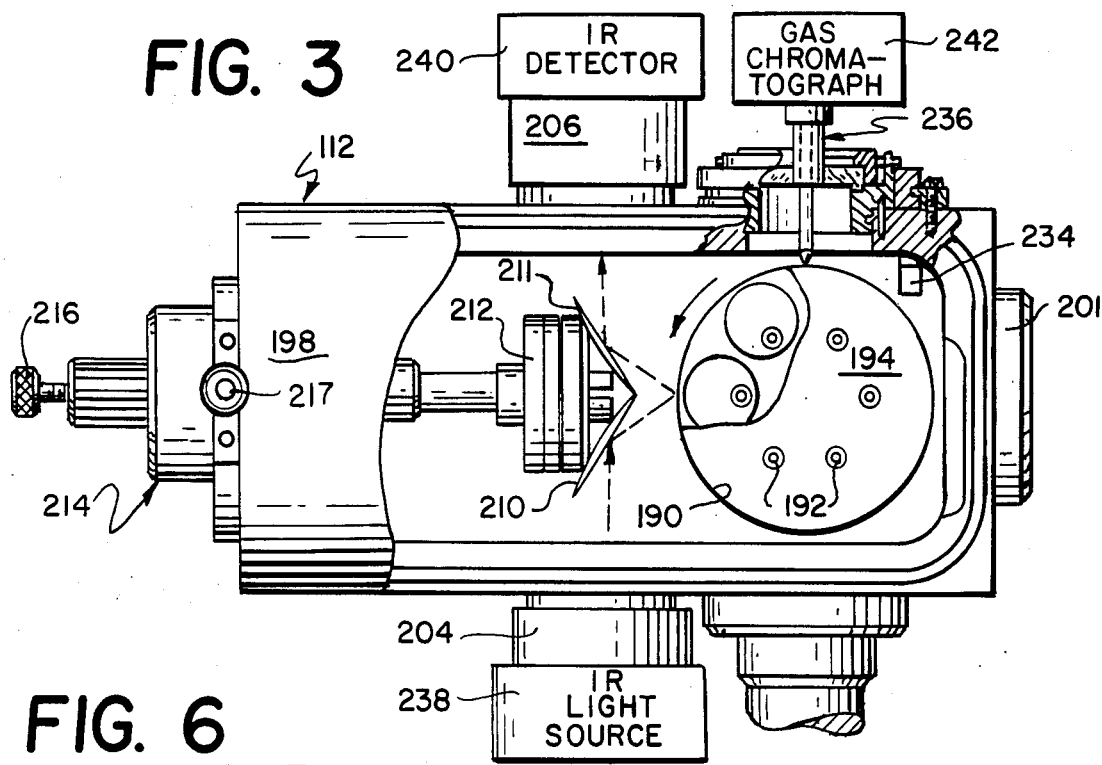
FIG. 3 is a partially cutaway top plan view of the matrix isolation apparatus of FIG. 2.
Figure 6:
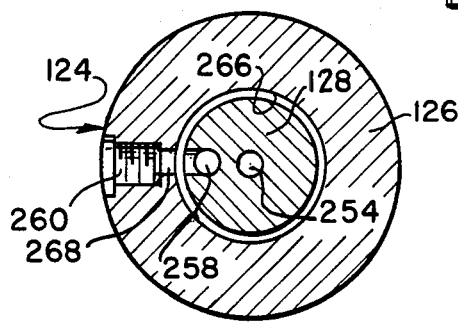
FIG. 6 is a sectional view of the matrix isolation apparatus of FIG. 4 taken along sight line 6—6 therein.
Figure 7:
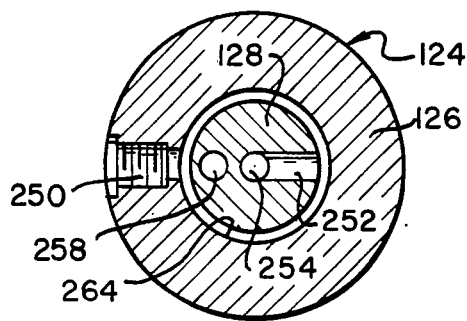
FIG. 7 is a sectional view of the matrix isolation apparatus of FIG. 4 taken along sight line 7—7 therein.
Figure 8:
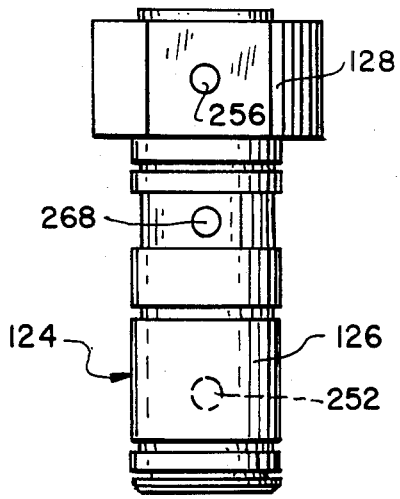

The sample collection chamber 112 is of a generally flat, rectangular shape as shown in FIGS. 2 and 3, the latter of which is a partially cutaway top plan view thereof. A gas chromatograph 242 is coupled to the sample collection chamber 112 by means of a sample delivery nozzle 236. The gas chromatograph 242 provides the sample to be analyzed to the sample collection chamber 112 via the sample delivery nozzle 236 for deposit upon the lateral, circular surface of the rotating specular carousel 190. Positioned immediately below and above the specular carousel 190 are lower and upper shields 193, 194 for reducing the amount of room temperature radiation incident upon the specular carousel 190. The lower and upper shields 193, 194 are maintained in position and coupled to each other by means of a plurality of mounting screws 192 which pass through holes (not shown) within the specular carousel 190. Room temperature radiation may enter the sample collection chamber 112 by means of an upper transparent cover 198 which preferably is comprised of glass to permit observation of the various components within the sample collection chamber 112 during operation of the matrix isolation apparatus 110. Positioned around the periphery of an upper portion of the sample collection chamber 112 and in abutting contact with its cover 198 is a gasket 202 for maintaining integrity of the vacuum seal therebetween.

Additional transparent ports may be provided in various lateral surfaces of the sample collection chamber 112 for observation and test analysis purposes. For example, a retainer assembly 201 containing a transparent window 200 is provided in a lateral surface of the sample collection chamber 112 to either permit the components within the sample collection chamber to be observed during operation or to provide another test sample analysis apparatus (not shown) access to the sample gas deposited upon the specular carousel.

Also mounted to the sample collection chamber 112 is a mirror support and positioning assembly 214. The mirror suport and positioning assembly 214 extends through a lateral wall of the sample collection chamber 112 and includes a mirror mount 212 securely positioned on one end thereof. Securely mounted to the mirror mount 212 are first and second parabolic reflecting mirrors 210, 211. An IR light source 238 is positioned adjacent to a first port 204 in a lateral portion of the sample collection chamber 112 for directing an IR beam onto the first parabolic reflecting mirror 210. The first parabolic mirror 210 directs the incident IR beam onto the lateral surface of the rotating specular carousel 190 immediately adjacent thereto. The specular carousel, in turn, reflects the IR beam incident thereon back to the second parabolic reflector 211 which, in turn, directs the reflected IR beam to an IR detector 240 via a second port 206 within the lateral surface of the sample collection chamber 112. The IR spectral absorption characteristics of the gas sample deposited upon the specular carousel 190 are included in the IR beam received by the IR detector 240. In a preferred embodiment, the specular carousel 190 is rotated in a counterclockwise direction as shown by the arrow in FIG. 3 although the improved matrix isolation apparatus 110 of the present invention will operate equally as well if the specular carousel is rotated in a clockwise direction. The IR detector 240 may be part of a conventional IR spectrometer for providing a spectrographic analysis of the sample material deposited upon the rotating specular carousel 190. Yet another reflecting mirror 234 is provided within the sample collection chamber 112 and is observable through the transparent cover 198 thereon for closely observing the operation of the sample delivery nozzle 236 in depositing the sample to be analyzed upon the moving, lateral surface of the specular carousel 190.

Referring specifically to FIG. 2, there is positioned within a lower portion of the sample collection chamber 112 a second aperture 227 adjacent to which is mounted to the sample collection chamber a flange 116 by means of a plurality of mounting bolts 196. Coupled to a lower end portion of the flange 116 is a threaded ring 176 having an inner threaded portion 180. The threaded ring 176 is maintained in position on the lower end of the flange 116 by means of a plurality of elongated mounting bolts 178. Positioned within the flange 116 along the length thereof and engaging the threaded inner portion 180 of the threaded ring 176 is the upper end portion of a housing assembly 120. The flange 116, the threaded ring 176, and the housing assembly 120 all have generally circular cross sections. A spacer 229 is positioned between the combination of the lower portion of the sample collection chamber 112 and upper end of the flange 116 and the upper end of the housing assembly 120. A pair of O-rings 231, 233 positioned between various of the aforementioned components ensure that a vacuum is maintained within the sample collection chamber 112. An intermediate portion of the housing assembly 120 is provided with a sprocket 162 around the circumference thereof.

A drive assembly 118 is coupled by means of the combination of a mounting bracket 171 and mounting bolt 178 to the lower end portion of the threaded ring 176. The drive assembly 118 includes a drive motor 172 coupled via a drive shaft 170 to a drive gear 166. Positioned substantially about the drive gear 166 and extending around the sprocket 162 mounted to the housing assembly 120 is a drive belt 164. The drive belt 164 is shown in sectional view at the left and right hand portions thereof and is respectively designated 164a and 164b adjacent to the sprocket 162 and drive gear 166. The drive belt 164 is of the endless type and may include a plurality of apertures (not shown) for engagement by respective teeth (also not shown) in the drive gear and sprocket, or may be a friction-type drive belt for engaging corresponding generally smooth portions of the drive gear and sprocket.

Rotational displacement of the drive gear 166 by means of the drive motor 172 causes the linear displacement of the drive belt 164 and resulting rotational displacement of the sprocket 162 and the housing assembly 120 to which it is mounted. The housing 120 is, in turn, coupled by means of its outer threaded portion 182 to the corresponding inner threaded portion 180 of the threaded ring 176, as previously described. With the threaded ring 176 securely coupled to the lower end of the flange 116, rotation of the housing assembly 120 will result in its linear displacement in a generally vertical direction within the flange 116. The use of a smooth drive belt for coupling the drive gear 166 to the sprocket 162 would allow for the use of an encoded disc (not shown) coupled to the housing 120 to provide precise information regarding the rotational position of the specular carousel 190.

Positioned within the housing assembly 120 and securely coupled to a lower, inner portion thereof is a lower cryostat duct/support shaft 184. Attached to an upper end portion of the lower cryostat duct/support shaft 184 is an upper cryostat duct/support shaft 186 which, in turn, is coupled at its upper end portion to and provides support for the specular carousel 190. Also mounted to the upper end portion of the lower cryostat duct/support shaft 184 is a support bracket 188 which also serves as a low temperature shield for the upper cryostat duct/support shaft 186 and which is coupled to and provides support for the specular carousel 190. By providing the cooling effect of a working fluid to the specular carousel 190 via the lower and upper cryostat ducts/support shafts 184, 186 the specular carousel may be maintained at a low temperature, e.g., 10°-20° K., for entrapment of the sample to be analyzed on the lateral surface of the specular carousel within a frozen matrix of an inert substance such as argon or krypton gas. The sample may thus be maintained in a neutral and noncontaminating matrix material over an extended period of time to permit high resolution infrared and other spectroscopic types of analyses of the sample. The first refrigerant stage at the upper end of the lower cryostat duct/support shaft 184 is maintained at a temperature of approximately 50° K. This refrigerant stage exhibits a relatively larger cooling capacity than the second refrigerant stage of the upper cryostat duct/support shaft 186 to which the specular carousel 190 is mounted.

It is to be noted that the specular carousel 190 coupled via the lower and upper cryostat ducts/support shafts 184, 186 to the housing assembly 120, rotation of the housing assembly will result in the rotational displacement of the specular carousel within the sample collection chamber 112. In addition, rotational displacement of the housing assembly 120 by means of the drive assembly 118 will result in the generally vertical, linear displacement of the specular carousel 190. This linear displacement of the specular carousel will permit the deposit of the sample material on the lateral surface thereof in the general form of a spiral, or helix, such that sample deposition and analysis may be carried out beyond a 360° rotation of the specular carousel to permit a larger sample of deposited material to be anaylzed. The amount of sample material deposited upon the specular carousel and which may be spectrographically analyzed is thus limited only by the circumference and the edge dimension of the disc-shaped specular carousel in the spiral sample depositon technique of the present invention.

Coupled to the mounting bracket 171 is the combination of an upper limit switch 167 and upper limit arm 173 and a lower limit switch 168 and lower limit arm 174. A contact pin 175 is mounted to the housing assembly 120 and is displaced upward and downward in response to the rotational and linear displacement of the housing assembly. When the contact pin 175 engages the lower limit arm 174, as shown in FIG. 2, the lower limit arm actuates the lower limit switch 168 for limiting the downward travel of the housing assembly 120. This is accomplished by the lower limit switch 168 providing an appropriate control signal to the drive assembly 118. Similarly, when the contact pin 175 engages the upper limit arm 173, the upper limit switch 167 is actuated by the upper limit arm for providing an appropriate control signal to the drive assembly 118 for terminating the upward displacement of the housing assembly. It is in this manner that the upper and lower displacement limits of the housing assembly 120 as well as of the specular carousel 190 coupled thereto may be established. In a preferred embodiment of the present invention, the vertical travel of the specular carousel 190 is limited to 0.175 inch.

Figure 4:
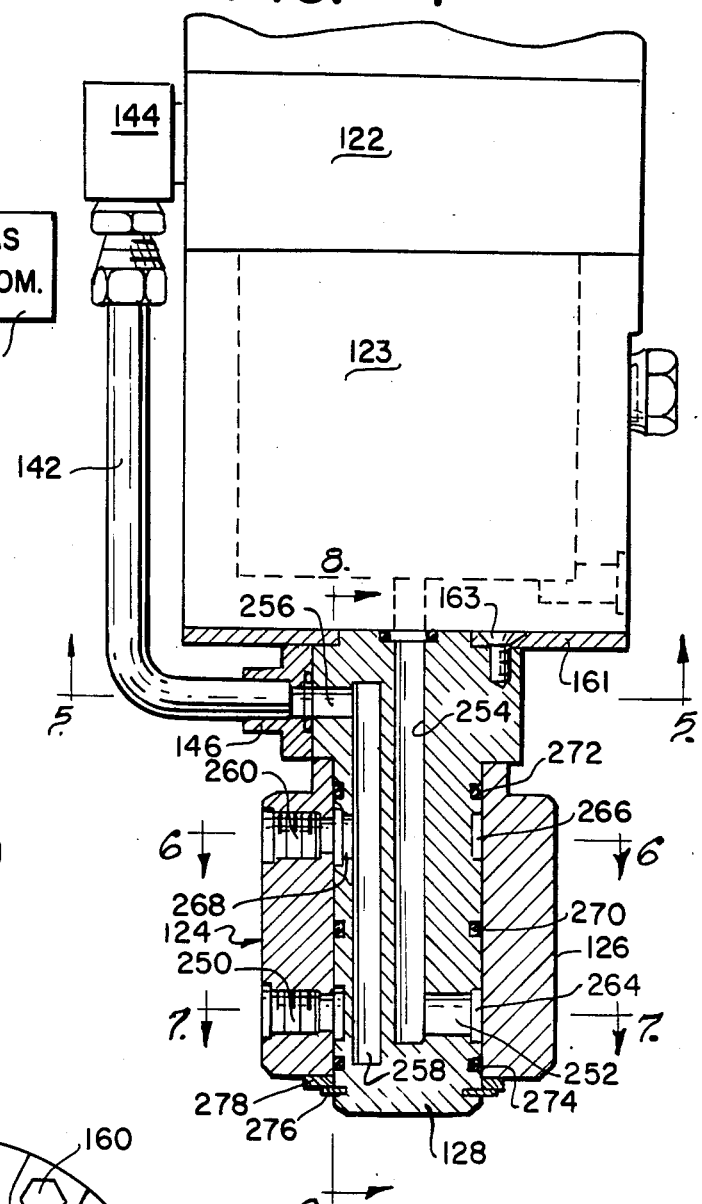
FIG. 4 is a vertical sectional view of a matrix isolation apparatus in accordance with the present invention showing in particular the details of the rotary union assembly utilized therein.
Figure 5:
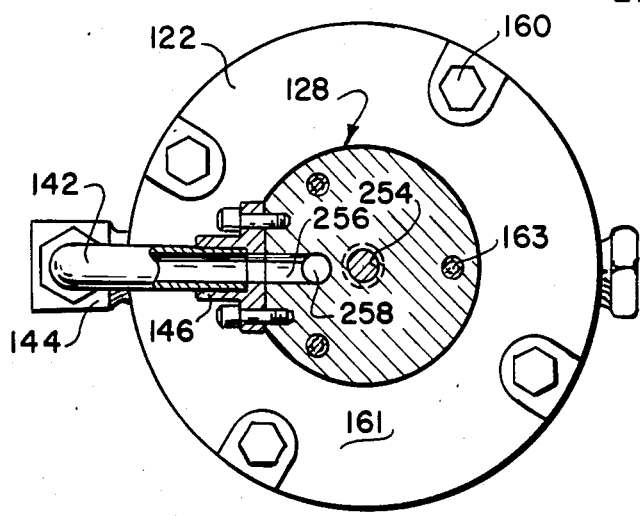
FIG. 5 is a sectional view of the matrix isolation apparatus of FIG. 4 taken along sight line 5—5 therein.

The lower end of the housing assembly 120 is coupled to the upper end portion of the expander module 122 by means of a plurality of coupling screws 160. The expander module 122 includes a working fluid chamber 123 therein and provides for the transfer of coolant from a circulating working fluid source 130 via a rotary union assembly 124 to the combination of the lower and upper cryostat ducts/support shafts 184, 186 and thence to the specular carousel 190 for reducing its temperature to approximately 10°–20° K. The details of the expander module 122 as well as of the rotary union assembly 124 are shown in FIG. 4 as well as in FIGS. 5, 6, 7 and 8 which are various sectional views thereof. The configuration and operation of this portion of the matrix isolation apparatus of the present invention will now be described with respect to these figures as well as FIG. 2.

The rotary union assembly 124 is coupled to a lower portion of the expander module 122 by means of a first plurality of coupling screws 160 (shown in FIG. 5), a mounting plate 161, and a second plurality of coupling screws 163. The rotary union assembly 124 includes a rotary gland 128 positioned within a generally annular shaped outer housing 126. The rotary gland 128 is free to rotate within the outer housing 126 and is maintained in position therein by means of the combination of a retention ring 276 and spacer 278.

The outer housing 126 of the rotary union assembly 124 is coupled by means of the combination of a working fluid inlet tube 132 and inlet coupler 136 and a working fluid outlet tube 134 and outler coupler 138 to a circulating working fluid source 130. The circulating working fluid source 130 may be conventional in design and operation and provides a recirculating working fluid such as helium to the rotary union assembly 124. The outer housing 126 includes an inlet duct 250 as well as an outlet duct 260 respectively coupled to the inlet tube 132 and inlet coupler 136 combination and to the outlet tube 134 and outlet coupler 138 combination. The outer lateral surface of the rotary gland 128 includes first and second annular slots 264, 266. A lower coupling duct 252 extends inward from the first annular slot 264 of the rotary gland 128 to a generally vertically oriented center channel 254 extending along the longitudinal axis of the rotary gland. Similarly, a relatively short upper coupling duct 268 extends inwardly from the second annular slot 266 in the surface of the rotary gland 128 to an offset channel 258 within the rotary gland. The offset channel 258 is generally parallel with the center channel 254 in the rotary gland 258, but is positioned intermediate the center channel and the outer circumference of the rotary gland. This arrangement permits a working fluid under pressure to be provided via the combination of the inlet tube 132 and inlet coupler 136 to the center channel 254 via the first annular slot 264 and lower coupling duct 252 regardless of the relative rotational position of the rotary gland 128 within the outer housing 126. In addition, with the lower coupling duct 252 always in communication with the first annular slot 264, a working fluid under pressure may be provided to the center channel 254 so as to flow upward therein during the rotational displacement of the rotary gland 128 within the outer housing 126 of the rotary union assembly 124.

A working fluid under pressure is thus provided to the center channel 254 and is allowed to flow into a working fluid chamber 123 within the expander module 122 with which the center channel is in communication. The working fluid thus reduces the temperature of the lower and upper cryostat ducts/support shafts 184, 186 which are coupled to and supported by the expander module 122 for cooling the specular carousel 190. A return line from the working fluid chamber 123 within the expander module 122 back to the rotary union assembly 124 is provided by the combination of an elbow coupler 144, a working fluid return line 142 and a coupler 146. The circulating working fluid thus returns at a reduced pressure via the working fluid return line 142 to an upper portion of the rotary gland 128 of the rotary union assembly 124. A return duct 256 connects the combination of the working fluid return line 142 and coupler 146 to the offset channel 258 to permit the working fluid to return to the circulating working fluid source 130 via the combination of the upper coupling duct 268, the second annular slot 266, the outlet duct 260, the outlet coupler 138, and the working fluid outlet tube 134. A plurality of O-rings 270, 272 and 274 are positioned in a sealed engagement between the rotary gland and outer housing portions of the rotary union assembly 124 to prevent leakage and escape of the circulating working fluid which flows therein.

Figure 9:
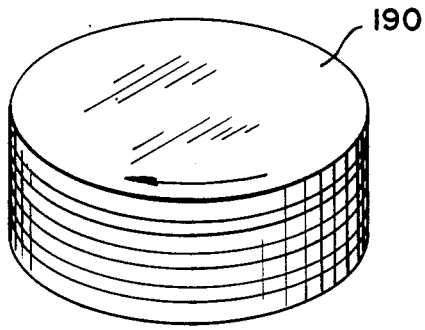
FIG. 9 is a perspective view of the specular carousel showing the manner in which the material to be spectrographically analyzed is deposited thereon in the form of a helical trace.

Referring to FIG. 9, there is shown a perspective view of the specular carousel 190 and the manner in which the sample material to be spectrographically analyzed is deposited on its lateral surface in the form of a helical trace. As shown in the figure, a single, continuous strip, or trace, of the sample to be analyzed has been deposited upon the lateral surface of the specular carousel as it undergoes rotational and translational displacement as described above.

There has thus been shown an improved gas sample collection apparatus for the matrix isolation of individual gas bands from a gas chromatographic separation and for the spectroscopic analysis of extended sample bands. A closed, circulating working fluid coupling arrangement permits the sample collector to be continuously rotated virtually any number of revolutions during the sample deposition and spectrographic analysis procedure. In addition, a rotational drive arrangement located exterior to the low temperature and evacuated portions of the matrix isolation apparatus provides for the rotational and linear displacement of the sample collector for permitting the collection and spectral analysis of increased amounts of sample material.

While particular embodiments of the present invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

The embodiments of the invention in which an exclusive property or privilege is claimed are defined as follows:

1. Apparatus for the spectroscopic analysis of a sample material condensed in the form of a solid matrix with an inert gas, wherein said sample material is irradiated by a beam of electromagnetic radiation incident thereon and said apparatus includes a working fluid source for providing a working fluid under high pressure for facilitating the condensation of said sample material at cryogenic temperatures, said apparatus comprising:

an evacuated chamber into which the sample material is directed in vapor form, said chamber having an aperture therein;

a specular disc positioned within said evacuated chamber and aligned with the beam of electromagnetic radiation, said disc having a lateral surface upon which the sample material vapor is directed and condenses;

rotational support means coupled to said evacuated chamber in sealed engagement about the aperture therein for supporting said specular disc and providing for the simultaneous rotational and generally vertical displacement of said specular disc whereby the sample material may condense on substantially the entire lateral surface of said specular disc in a helical trace, said rotatable support means including a cryogenic expander module coupled to said specular disc for maintaining said rotating specular disc at cryogenic temperatures; and rotary coupling means for connecting the working fluid source to said rotatable support means during multiple revolutions of said rotatable support means and for providing the working fluid under high pressure to said cryogenic expander module within said rotatable support means for facilitating condensation of the sample material on said rotating disc, said rotary coupling means including a fixed outer housing coupled to the working fluid source, a rotatable inner member positioned within said outer housing and fixedly coupled to said rotatable support means, a plurality of annular slots disposed between said fixed outer housing and said rotatable inner member, and seal means disposed in said annular slots between said outer housing and said inner member so as to form a high pressure seal for preventing a leakage and an escape of the working fluid.

2. The apparatus of claim 1 further comprising drive means coupled to said rotatable support means for rotationally and translationally displacing said support means.

3. The apparatus of claim 2 wherein said rotatable support means comprises the combination of a flange coupled to said evacuated chamber and a housing coupled to said specular disc and providing support therefor, wherein said flange and said housing have generally circular cross-sections and are coupled to each other in a movable manner.

4. The apparatus of claim 3 wherein said drive means is coupled to said housing for the rotational displacement thereof and wherein said housing undergoes translation relative to said flange when thus rotated.

5. The apparatus of claim 4 wherein said flange is a hollow cylinder aligned with the aperture of said evacuated chamber and having a threaded inner surface and said housing includes a threaded outer surface adapted for engagement with the threaded inner surface of said flange to permit relative rotation between said flange and said housing and translation of said housing along said flange when thus rotated.

6. The apparatus of claim 5 wherein said drive means includes the combination of a drive motor and drive belt and wherein said drive belt is positioned around a portion of the outer surface of said housing and in engagement therewith for rotationally displacing said housing.

7. The apparatus of claim 1 wherein said working fluid flows in a continuous manner through said rotary coupling means from the working fluid source and returns thereto.

8. The apparatus of claim 1 wherein said inner member is a rotary gland positioned within said outer housing and said seal means is disposed about said rotary gland so as to prevent leakage and escape of the working fluid as said rotary gland rotates relative to said fixed outer housing.

9. The apparatus of claim 8 wherein said outer housing includes inlet and outlet ducts for respectively receiving the working fluid from and returning the working fluid to the working fluid source and wherein said rotary gland includes inlet and outlet flow channels aligned respectively with the inlet and outlet ducts of said outer housing during the 360° rotational displacement of said rotary gland.

10. The apparatus of claim 9 wherein the inlet and outlet flow channels of said rotary gland respectively include first and second annular slots in the outer surface thereof in communication with respective first and second flow channels positioned within said rotary gland wherein said first and second flow channels are in communication with said working fluid chamber and said first and second annular slots are respectively in communication with the inlet and outlet ducts of said outer housing.

11. The apparatus of claim 10 wherein said seal means includes a plurality of sealing rings positioned between the rotary gland and the outer housing of said rotary coupling means for preventing the leakage and escape of the working fluid.

* * * * *

UNITED STATES PATENT AND TRADEMARK OFFICE
CERTIFICATE OF CORRECTION

PATENT NO. : 4,688,936
DATED : August 25, 1987
INVENTOR(S) : Gerald T. Reedy

It is certified that error appears in the above—identified patent and that said Letters Patent is hereby corrected as shown below:

On the title page, column 2, second line from the bottom, insert a comma (,) after "improved".

Column 5, line 19, "conventionally" should be -- conventional --

Column 6, line 46, after "within", "the" should be -- a --.

Signed and Sealed this

Fifteenth Day of December, 1987

Attest:

DONALD J. QUIGG

*Attesting Officer*  *Commissioner of Patents and Trademarks*